United States Patent
Paul

(10) Patent No.: US 8,580,237 B2
(45) Date of Patent: Nov. 12, 2013

(54) HAIR STYLING COMPOSITION

(75) Inventor: Prem Kumar Cheyalazhagan Paul, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 396 days.

(21) Appl. No.: 12/664,062

(22) PCT Filed: Jun. 11, 2008

(86) PCT No.: PCT/EP2008/057316
§ 371 (c)(1),
(2), (4) Date: Dec. 11, 2009

(87) PCT Pub. No.: WO2009/003808
PCT Pub. Date: Jan. 8, 2009

(65) Prior Publication Data
US 2010/0172855 A1    Jul. 8, 2010

(30) Foreign Application Priority Data
Jul. 3, 2007  (EP) ..................................... 07111634

(51) Int. Cl.
*A61K 8/00* (2006.01)
*A61K 8/18* (2006.01)
*A61K 8/72* (2006.01)
*A61Q 5/00* (2006.01)
*A61Q 9/00* (2006.01)
*A61Q 7/00* (2006.01)

(52) U.S. Cl.
USPC ....................................... 424/70.11; 424/70.1

(58) Field of Classification Search
USPC ............................................ 424/70.1, 70.11
See application file for complete search history.

(56) References Cited

U.S. PATENT DOCUMENTS 6,569,407 B1  5/2003 Suria et al. ....................... 424/47
2006/0263315 A1  11/2006 Plos et al. .................... 424/70.7

FOREIGN PATENT DOCUMENTS

DE  44 36 065  4/1996
EP  1 707 241  10/2006
EP  0 791 350  4/2008

OTHER PUBLICATIONS

Corycosmetics.com. http://www.corycosmetics.com/cosmetic_ingredients_glossary.htm. Aug. 2003.*
Merriam-Webster: "Definition of triethanolamine". Accessed 2012.*
Prathna et al. (Colloids Surf B Biointerfaces. Jan. 1, 2011;82(1):152-9. doi: 10.1016/j.colsurfb.2010.08.036. Epub Sep. 15, 2010).*
Hogg et al. (TRENDS in Biochemical Sciences vol. 28 No. 4 Apr. 2003:210-214).*
Pati et al. (Langmuir 2009, 25, 67-70).*
Shakhashiri, Bassam (Chemical Demonstrations: A Handbook for Teachers of Chemistry. vol. 3. Madison, Wisconsin:The Board of Regents of the University of Wisconsin. The University of Wisconsin Press. 1989. See p. 68).*
Sierra Chemical Co. Triethanolamine 99%. http://www.sierrachemicalcompany.com/index.php?page=shop.product_details&flypage=flypage.tpl&category_id=6&product_id=189&option=com_virtuemart&Itemid=2. Accessed 2013).*
Abstract of EP 0 791 350 B2—published Apr. 5, 2006.
Abstract of DE 44 36 065—published Apr. 11, 1996.

* cited by examiner

*Primary Examiner* — Jeffrey S. Lundgren
*Assistant Examiner* — Chris Simmons
(74) *Attorney, Agent, or Firm* — Ronald A. Koatz

(57) ABSTRACT

A hair styling composition comprising: i) an amino acid comprising an urea moiety in its side chain; ii) a solvent for component i).

6 Claims, No Drawings

HAIR STYLING COMPOSITION

The invention relates to a hair styling compositions and a method of styling. The invention is particularly advantageous in relation to hair straightening.

The current hair market has a wide range of styling products. A common way to retain a particular hairstyle is to apply a hairspray, mousse, gel, lotion or wax. Good holding power is one attribute a consumer looks for in such styling products, as is a natural feel to the hair. The styling materials in these compositions are generally film forming agents, resins, gums, and/or adhesive polymers The styling market can be classified in various sub-sets based on the desired styling effect; one such sub-set is products for straightening the hair.

A problem with straightened hair is that once the straightening process has taken place the hair tends to increase in volume causing it to appear fluffy, this is especially troublesome in humid conditions.

The present invention has now found that compositions containing certain amino acids can be used to impart humidity resistance to straightened hair and thus retain its style.

The present invention relates to a non-permanent hair styling composition comprising:
i) an amino acid comprising an urea moiety in its side chain;
ii) a solvent for component i).

This invention also relates to a method of non-permanently styling hair by application of the above composition to hair.

Compositions of the invention comprise a straightening active preferably selected from an amino acid or salt thereof having the following formula:

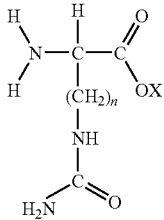

where X is a suitable cation, preferably H.

n is a number from 1 to 8; more preferably a number from 2 to 4, most preferably x 3 is and the straightening active is citrulline The level of straightening compound present in the total formulation is from 0.01 wt % to 20 wt %, more preferably from 0.1 wt % to 10 wt %, most preferably from 0.8 wt % to 5 wt %.

Compositions according to the invention preferably do not comprise compounds capable of breaking the bonds of the hair. Such compound can be known as reducing agents or perming agents.

Compositions of the invention comprise a solvent for the straightening compound.

Preferred solvents are organic acids and salts thereof, more preferred are α-hydroxy acid acids and salts thereof, of particular interest are bis (α-hydroxy acids) and/or their salts.

The α-hydroxy acid can comprise one or more carboxylic acid groups, at least one of these carboxylic acid groups should have an α-hydroxy group.

α-Hydroxy acids which are of most importance for use with the present invention are citric acid and tartaric acid and/or their salts.

The amount of solvent is preferably from 0.1 to 20 wt % in the total formulation, more preferably from 0.5 to 15 wt %, most preferably from 1 to 10 wt %.

The weight ratio of straightening compound to solvent is preferably from 5:1 to 1:100, preferably from 3:1 to 1:10, most preferably from 1:1 to 1:5.

In many aspects of this invention it is highly desirable if the compositions further comprise a styling aid.

Particularly useful as styling aids with this invention are hair styling polymers. Hair styling polymers are well known articles of commerce and many such polymers are available commercially which contain moieties which render the polymers cationic, anionic, amphoteric or nonionic in nature. The polymers may be synthetic or naturally derived.

Styling aids such as vinylic polymer are preferred, in particular block copolymers.

The amount of the hair styling polymer may range from 0.1 to 10%, preferably 0.5 to 8%, more preferably 0.75 to 6% by weight based on total weight of the composition.

Examples of anionic hair styling polymers are:
copolymers of vinyl acetate and crotonic acid;
terpolymers of vinyl acetate, crotonic acid and a vinyl ester of an alpha-branched saturated aliphatic monocarboxylic acid such as vinyl neodecanoate;
copolymers of methyl vinyl ether and maleic anhydride (molar ratio about 1:1) wherein such copolymers are 50% esterified with a saturated alcohol containing from 1 to 4 carbon atoms such as ethanol or butanol;
acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate);
glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Specific examples of suitable anionic hair styling polymers are:
RESYN® 28-2930 available from National Starch (vinyl acetate/crotonic acid/vinyl neodecanoate copolymer);
ULTRAHOLD® 8 available from BASF (CTFA designation Acrylates/acrylamide copolymer);
the GANTREZ®ES series available from ISP corporation (esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are cross-linked silicone resins or gums. Specific examples include rigid silicone polymers such as those described in EP-A-0240350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic hair styling polymers are:
copolymers of N-vinylpyrrolidone and dimethylaminoethyl methacrylate, available from ISP Corporation as Copolymer 845, Copolymer 937 and Copolymer 958;
copolymers of N-vinylpyrrolidone and dimethylaminopropylacrylamide or methacrylamide, available from ISP Corporation as Styleze® CC10;
copolymers of N-vinylpyrrolidine and dimethylaminoethyl methacrylate;
copolymers of vinylcaprolactam, N-vinylpyrrolidone and dimethylaminoethylmethacrylate;
Polyquaternium-4 (a copolymer of diallyldimonium chloride and hydroxyethylcellulose);
Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;
Polyquaternium-16 (formed from methylvinylimidazolium chloride and vinylpyrrolidone), available from BASF as Luviquat® FC 370, FC 550, FC 905 and HM-552;
Polyquaternium-46 (prepared by the reaction of vinylcaprolactam and vinylpyrrolidone with methylvinylimidazolium methosulphate), available from BASF as Luviquat®Hold.

Examples of suitable naturally-derived hair styling polymers include shellac, alginates, gelatins, pectins, cellulose derivatives and chitosan or salts and derivatives thereof. Commercially available examples include Kytamer® (ex Amerchol) and Amaze® (ex National Starch).

Also suitable for use as optional components in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macrografted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

With certain of the above-described polymers it may be necessary to neutralise some acidic groups to promote solubility/dispersibility. Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanolamine (DIPA); triisopropanolamine (TIPA); and dimethyl stearamine (DMS). A long chain amine neutralising agent such as stearamidopropyl dimethylamine or lauramidopropyl dimethylamine may be employed, as is described in U.S. Pat. No. 4,874,604. Also suitable are inorganic neutralisers, examples of which include sodium hydroxide, potassium hydroxide and borax. Mixtures of any of the above neutralising agents may be used. Amounts of the neutralising agents will range from about 0.001 to about 10% by weight of the total composition.

Compositions of the present invention are formulated into hair care compositions, especially products with hair styling claims. The compositions are preferably for use in styling human hair and, more preferably, they are packaged and labeled as such.

It is preferred if the products are left on hair after application and not immediately washed off (within 30 minutes of application). Such products are called "leave on" formulations.

Preferred product forms are leave on formulations such as gels, mousses, sprays and aerosols.

It is preferable if the pH at 30° C. of the composition is from 2.5 to 9, more preferably above 4, most preferably from 5 to 8.

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Compositions according to the invention comprise a buffer or pH adjuster. Preferred buffers or pH adjusters include weak acids and bases such glycine/sodium hydroxide, citric acid, lactic acid, succinic acid, acetic salt and salts thereof. Frequently a mixture of buffering system is used such as sodium citrate and citric acid.

Carriers suitable for use with hair care compositions of the present invention include, for example, those used in the formulation of hair sprays, mousses, tonics, waters, creams gels, shampoos, conditioners, and rinses. The choice of appropriate carrier will depend on the particular product to be formulated. The carriers used herein can include a wide range of components conventionally used in hair care compositions. The carriers can contain a solvent to dissolve or disperse the styling compound being used, with water, the $C_1$-$C_6$ alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Hair styling creams or gels also typically contain a structurant or thickener, typically in an amount of from 0.01% to 10% by weight.

Suitable spray containers are well known in the art and include conventional, non-aerosol pump sprays i.e., "atomisers", aerosol containers or cans having propellant, as described above, and also pump aerosol containers utilising compressed air as the propellant.

The formulation may include conditioning materials such as surfactants, cationic conditioners suitable for hair, quaternary silicone polymers, silicone based conditioners and their emulsions, and amino functional silicones and their emulsions.

Further general ingredients suitable for all product forms include, sun-screening agents, anti-dandruff actives, carboxylic acid polymer thickeners for hair shampoo and conditioner compositions and emulsifiers for emulsifying the various carrier components of the compositions of the invention.

The compositions of the present invention may also contain adjuncts suitable for hair care. Generally such ingredients are included individually at a level of up to 2, preferably up to 1 wt % of the total composition. Suitable hair care adjuncts, include amino acids, sugars and ceramides.

The method of the invention comprises applying compositions of the invention to the hair preferably followed by a heating step. The hair should be heated to a temperature above 100° C., preferably above 150° C., more preferably above 180° C.

The following non-limiting Examples further illustrate the preferred embodiments of the invention. All percentages referred to in the examples and throughout this specification are by weight based on total weight unless otherwise indicated.

EXAMPLES

Hair switches were either soaked in the solutions listed below for 1 hour or switches were dosed with the product using a syringe. The treated hair switches were then styled straight using wet to dry hot irons. After the final iron pass the switches were combed at least 5 times. The switches were left for 3 hours at 30° C. and 80% relative humidity. The results are shown in table 1.

TABLE 1

| Formulation | Final area in mm^2 after 3 hrs of 80% RH at 30 C. |
|---|---|
| Water | 13422 |
| 2% citrulline solution soaked | 11897 |
| 2% citric acid solution soaked ~pH 3 | 9669 |
| 0.5 gms of 2% citric acid solution dosed ~pH 3 | 9433 |
| 0.5 gms of 2% citrulline in 2% citric acid solution dosed ~pH 3 | 5900 |
| 2% citrulline in 2% citric acid solution soaked ~pH 3 | 5256 |
| 0.5 gms of 2% citrulline in 2% citric acid solution + triethanolamine (TEA) to ~pH 6 dosed | 3509 |

The results show that Examples of the invention with citrulline exhibit better straightening than comparative Examples containing citric acid or water. Furthermore, better straightening is achieved at pH 6 compared with pH 3.

A formulation according to the invention is given below:

| Chemical Name | Example 2 |
|---|---|
| Cetearyl Alcohol -CSA | 5.00 |
| Cetrimonium Chloride - CTAC | 1.30 |
| Glyceryl Stearate | 0.60 |
| Methyl Paraben | 0.20 |
| Mineral Oil | 0.30 |
| Glycerin | 1.0 |
| DC 1784 silicone | 1.30 |
| Perfume | 0.30 |
| Citrulline | 1 |
| Citric acid | 3 |
| Triethanolamine (TEA) | to pH 6 |
| Water and minors | To 100% |

The invention claimed is:

1. A non-permanent hair styling composition consisting essentially of:
   i) from 0.01 to 5% by wt. of total composition of an amino acid or salt thereof comprising an urea moiety in its side chain having the following formula;

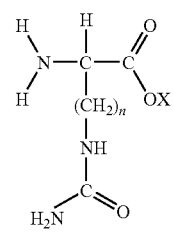

where n is a number from 1 to 8 and X is H or a suitable cation; and
   ii) from 0.1 to 20% by wt. of total composition of a solvent for component i) wherein the solvent comprises citric acid, wherein the composition has a pH from 5 to 8 at 30° C.
wherein said amino acid is a straightening active; and iii) about 0.001 to 10% by wt. total composition of a neutralizing agent which together with the solvent of (ii) maintains said pH at pH of 5-8,
wherein said composition contains no perming agent which breaks the bonds of the hair at said pH.

2. A non-permanent hair styling composition according to claim 1 in which the straightening active is citrulline.

3. A non-permanent styling composition according to claim 1 which further comprises a hair styling polymer.

4. A method of non-permanently styling hair comprising the step of applying a composition according to claim 1 to the hair.

5. A method of non-permanently styling hair according to claim 4, wherein the step of applying the composition to the hair is followed by heating the hair to a temperature above 100° C.

6. A method of non-permanently styling hair according to claim 5 in which the hair is heated to a temperature above 150° C.

\* \* \* \* \*